United States Patent
Surti

(10) Patent No.: US 8,696,550 B2
(45) Date of Patent: Apr. 15, 2014

(54) ENDOSCOPE SHEATH

(75) Inventor: Vihar C. Surti, Winston-Salem, NC (US)

(73) Assignee: Cook Medical Technologies LLC, Bloomington, IN (US)

(*) Notice: Subject to any disclaimer, the term of this patent is extended or adjusted under 35 U.S.C. 154(b) by 121 days.

(21) Appl. No.: 12/968,879

(22) Filed: Dec. 15, 2010

(65) Prior Publication Data
US 2011/0313242 A1    Dec. 22, 2011

Related U.S. Application Data

(60) Provisional application No. 61/288,060, filed on Dec. 18, 2009, provisional application No. 61/288,050, filed on Dec. 18, 2009, provisional application No. 61/288,259, filed on Dec. 18, 2009.

(51) Int. Cl.
*A61B 1/00* (2006.01)

(52) U.S. Cl.
USPC ........... 600/129; 600/107; 600/114; 600/121; 600/123

(58) Field of Classification Search
USPC .................. 600/106–107, 121–125, 127, 129
See application file for complete search history.

(56) References Cited

U.S. PATENT DOCUMENTS

| | | | | |
|---|---|---|---|---|
| 3,173,414 A | * | 3/1965 | Guillant | 600/565 |
| 3,703,169 A | * | 11/1972 | Ouchi | 600/107 |
| 5,386,817 A | * | 2/1995 | Jones | 600/104 |
| 6,071,233 A | * | 6/2000 | Ishikawa et al. | 600/104 |
| 6,605,033 B1 | | 8/2003 | Matsuno | |
| 6,689,051 B2 | | 2/2004 | Nakada et al. | |
| 6,878,106 B1 | * | 4/2005 | Herrmann | 600/104 |
| 7,081,097 B2 | * | 7/2006 | Martone et al. | 600/562 |
| 8,075,478 B2 | * | 12/2011 | Campos | 600/139 |
| 2001/0049509 A1 | | 12/2001 | Sekine et al. | |
| 2002/0156344 A1 | | 10/2002 | Pasricha et al. | |
| 2003/0088154 A1 | | 5/2003 | Ishibiki et al. | |
| 2004/0230097 A1 | * | 11/2004 | Stefanchik et al. | 600/127 |
| 2004/0267092 A1 | | 12/2004 | Ishibiki | |
| 2005/0059890 A1 | | 3/2005 | Deal et al. | |
| 2005/0222495 A1 | | 10/2005 | Okada et al. | |
| 2005/0288549 A1 | | 12/2005 | Mathis | |
| 2006/0258910 A1 | | 11/2006 | Stefanchik et al. | |
| 2006/0264705 A1 | | 11/2006 | Adams et al. | |

(Continued)

FOREIGN PATENT DOCUMENTS

DE    20 2008 007 774 U1    9/2008
EP    1 284 120 A1    2/2003

(Continued)

OTHER PUBLICATIONS

Invitation to Pay Additional Fees & PCT Communication Relating to the Results of the Partial International Search for corresponding case PCT/US2010/060447; Apr. 15, 2011; 6p.

*Primary Examiner* — Matthew J Kasztejna
(74) *Attorney, Agent, or Firm* — Brinks Gilson & Lione

(57) ABSTRACT

An endoscope sheath is provided for advancing medical devices into the anatomy of a patient. The endoscope sheath includes at least one lumen that may be used to advance devices alongside an endoscope. The endoscope sheath may include an endoscope cap configured to mate with the lumen. The endoscope may include one or more coupling members configured to mate with the openings of the lumen.

15 Claims, 13 Drawing Sheets

(56) References Cited

U.S. PATENT DOCUMENTS

| | | |
|---|---|---|
| 2007/0142709 A1 | 6/2007 | Martone et al. |
| 2008/0177135 A1* | 7/2008 | Muyari et al. ............... 600/104 |
| 2008/0249354 A1* | 10/2008 | Muyari et al. ............... 600/104 |
| 2009/0259172 A1 | 10/2009 | Yamaoka et al. |
| 2010/0113878 A1 | 5/2010 | Kawano |

FOREIGN PATENT DOCUMENTS

| | | |
|---|---|---|
| EP | 1 582 138 B1 | 10/2005 |
| EP | 1 721 567 A2 | 11/2006 |
| WO | WO 2007/091523 A1 | 8/2007 |

* cited by examiner

ENDOSCOPE SHEATH

CROSS-REFERENCE TO RELATED APPLICATIONS

The present application claims the benefit of the following applications: U.S. Provisional Application No. 61/288,060, titled "Endoscope Sheath", filed Dec. 18, 2009, the entirety of which is hereby incorporated by reference; U.S. Provisional Application No. 61/288,050, titled "Endoscope Cap With Ramp", filed on Dec. 18, 2009, the entirety of which is hereby incorporated by reference; and U.S. Provisional Application No. 61/288,259, titled "Advancing System and Method of Use Thereof", filed Dec. 18, 2009, the entirety of which is hereby incorporated by reference.

TECHNICAL FIELD

The present invention relates to medical devices, and more particularly to an endoscope sheath.

BACKGROUND OF THE INVENTION

Physicians use endoscopes during minimally invasive procedures to visualize the patient anatomy, diagnose various conditions, and deliver instrumentation to the treatment site. Devices are typically delivered via a working channel of the endoscope, which generally ranges from about 2.0 to 3.5 mm in diameter, and may be used to introduce catheters and other elongate devices, including forceps, scissors, brushes, snares, and baskets. Larger working channels of 5.0 mm in diameter are available in certain specialized endoscopes, and may be used to pass relatively large devices or provide capability for improved aspiration or decompression. Some devices, however, are simply too large to pass through available endoscopes. Moreover, the specialized endoscopes with larger working channels can be expensive, as well as difficult to intubate due to increased rigidity and outer diameter.

Devices too large for the endoscope working channel must be introduced through an alternate, and often more invasive procedure, such as laparoscopy or open surgery. Laparoscopic surgery involves creating 0.5-1.5 cm incisions in a patient's abdominal wall so that a laparoscope and other instruments can be introduced into the abdominal and pelvic cavities. Open surgery generally involves creating one or more long incisions in a patient, followed by extensive muscle stripping, prolonged retraction of tissues, denervation and devascularization of tissue. While effective at introducing larger devices, laparoscopic and open surgical procedures can increase the risk of complications and trauma to the patient, as well as extend recovery time and hospital stays.

What is needed are devices and methods for endoscopic introduction of medical devices too large for the endoscope working channel without necessitating the use of invasive procedures. Specifically, devices and methods are needed for introduction of medical devices alongside and external to an endoscope.

SUMMARY

The present disclosure generally provides an endoscope sheath. The sheath may be used to aid in the delivery of devices to a selected target area in the anatomy of a patient. Preferably, the sheath is used in conjunction with a system for advancing devices alongside an endoscope. In one embodiment, the sheath can be used with a tether system used for pulling devices down alongside an endoscope. The tether system may include a guiding member for advancing devices beyond a distal portion of the endoscope. In another embodiment, the sheath may be used in conjunction with an endoscope cap used for deflecting devices into a selected target anatomy. In another embodiment, the sheath, the tether system, and the endoscope cap may be used in combination.

In one aspect, an endoscope sheath is provided. The endoscope sheath includes a first proximal end, a first distal end, and a first lumen extending from the first proximal end to the first distal end. The first lumen is configured to receive an endoscope. The endoscope sheath further includes a second lumen having a second proximal end and second distal end, wherein the second lumen is configured to receive a medical device. The endoscope sheath further includes a first aperture and a second aperture, wherein the first aperture is disposed at the second proximal end and wherein the second aperture is disposed at the second distal end. Preferably, the first aperture is located distal to the first proximal end, and the second aperture is located proximal to the first distal end.

In one embodiment, the endoscope sheath may include an endoscope cap. The cap may be integral with the sheath, or alternatively, may be detachable. The endoscope cap may include a first coupling member mated with the second lumen of the endoscope sheath at the second distal end. The first coupling member may include a first coupling member proximal portion and a first coupling member distal portion. The first coupling member may further include a first coupling member lumen extending from the first coupling member proximal portion to the first coupling member distal portion, with the lumen open at both ends. The first coupling member lumen preferably is configured to receive the medical device delivered through the second lumen. In one embodiment, the first coupling member proximal portion includes an outer surface configured to frictionally engage an inner surface of the endoscope sheath second lumen. Preferably, the first coupling member is comprised of a rigid material.

In another embodiment, the endoscope sheath may include a first coupling member mated with the second lumen at the second distal end. The endoscope sheath may include a second coupling member mated with the second lumen at the second proximal end. The first coupling member may include a body and a first coupling member lumen extending from a first coupling member proximal portion to a first coupling member distal portion. Preferably, the first coupling member lumen is open at both ends. The first coupling member may be comprised of a rigid material. Likewise, the second coupling member may include a body and a second coupling member lumen extending from a second coupling member proximal portion to a second coupling member distal portion. Preferably, the second coupling member lumen is open at both ends. The second coupling member may be comprised of a rigid material.

In another embodiment, the endoscope sheath includes a first proximal end, a first distal end, and a first lumen extending from the first proximal end to the first distal end. The first lumen may be configured to receive an endoscope. The endoscope sheath includes a second lumen having a second proximal end and a second distal end, wherein the second lumen is configured to receive a medical device. The endoscope sheath further includes a first aperture and a second aperture, wherein the first aperture is disposed at the second proximal end and wherein the second aperture is disposed at the second distal end. The first aperture is located distal to the first proximal end, and the second aperture is located proximal to the first distal end. The endoscope sheath further includes a first coupling member mated with the second lumen at the second distal end, and a second coupling member mated with the second lumen at the second proximal end.

In another aspect, a method is provided for delivering a medical device to an internal site of treatment. The method uses an endoscope and an endoscope sheath. The endoscope sheath includes a first proximal end, a first distal end, and a first lumen extending from the first proximal end to the first distal end. The first lumen is configured to receive the endoscope. The endoscope sheath further includes a second lumen having a second proximal end and second distal end, wherein the second lumen is configured to receive the medical device. The endoscope sheath further includes a first aperture and a second aperture, wherein the first aperture is disposed at the second proximal end and wherein the second aperture is disposed at the second distal end. The method includes advancing the medical device into the first aperture, advancing the medical device through the second lumen, and advancing the medical device to and out of the second aperture. In one embodiment, the medical device is advanced through the second lumen by pushing the device therethrough.

Other systems, methods, features and advantages will be apparent to one with skill in the art upon examination of the following figures and detailed description. It is intended that all such additional systems, methods, features and advantages be included within this description, be within the scope of the invention, and be protected by the following claims.

BRIEF DESCRIPTION OF THE DRAWINGS

The system may be better understood with reference to the following drawings and description. The components in the figures are not necessarily to scale, emphasis instead being placed upon illustrating the principles of the invention. Moreover, in the figures, like referenced numerals designate corresponding parts throughout the different views.

DEFINITIONS

Unless otherwise defined, all technical and scientific terms used herein have the same meaning as commonly understood by one of ordinary skill in the art to which this invention pertains. In case of conflict, the present document, including definitions, will control. Preferred methods and materials are described below, although methods and materials similar or equivalent to those described herein can be used in the practice or testing of the present invention. The materials, methods, and examples disclosed herein are illustrative only and not intended to be limiting.

The terms "comprise(s)," "include(s)," "having," "has," "can," "contain(s)," and variants thereof, as used herein, are intended to be open-ended transitional phrases, terms, or words that do not preclude the possibility of additional acts or structures. The present invention also contemplates other embodiments "comprising," "consisting of" and "consisting essentially of," the embodiments or elements presented herein, whether explicitly set forth or not.

The term "biocompatible," as used herein, refers to a material that is substantially non-toxic in the in vivo environment of its intended use, and that is not substantially rejected by the patient's physiological system. A biocompatible structure or material, when introduced into a majority of patients, will not cause an undesirably adverse, long-lived or escalating biological reaction or response. Such a response is distinguished from a mild, transient inflammation which typically accompanies surgery or implantation of foreign objects into a living organism.

The term "distal," as used herein, refers to a direction that is generally towards a target site within a patient's anatomy during a medical procedure.

The term "proximal," as used herein, refers to a direction that is generally towards a physician during a medical procedure.

The term "stricture," as used herein, refers to any narrowing of a bodily lumen in relation to an adjacent lumen portion.

DETAILED DESCRIPTION

Figure 1:
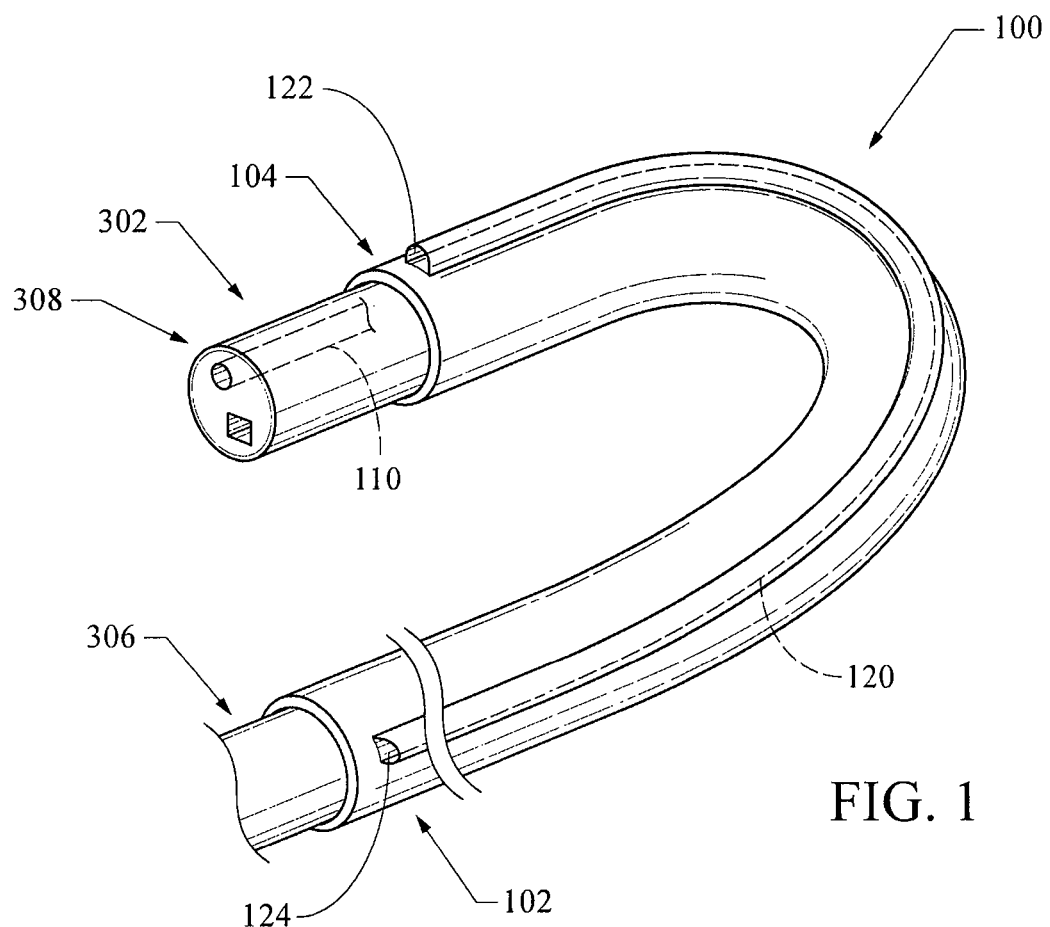
FIG. 1 depicts endoscope sheath 100.

FIG. 1 depicts endoscope sheath 100 disposed over an endoscope 302, the endoscope having a proximal portion 306 and a distal portion 308. Sheath 100 includes a proximal portion 102 and a distal portion 104. The sheath extends from the endoscope proximal portion to the endoscope distal portion. The sheath includes a first lumen 110 for the endoscope and a second lumen 120 for delivering devices alongside the endoscope. In some embodiments, the sheath may include a plurality of lumens for delivering devices alongside the endoscope. Lumen 120 extends from proximal portion 102 to distal portion 104 and has a distally located aperture 122, and a proximally located aperture 124.

The sheath may have a range of widths and lengths depending on the size of the endoscope to be used. In general, the sheath length ranges from about 100 cm to about 200 cm; and the sheath has a wall thickness of between about 0.1 mm to about 8 mm. The maximum diameter of lumen 120 generally ranges from about 2 mm to about 30 mm, preferably about 4 mm to about 25 mm, more preferably about 6 mm to about 20 mm, most preferably 8 to about 15 mm. In some embodiments, the sheath is comprised of an elastic material wherein lumen 120 may have a unexpanded diameter and an expanded diameter, with the expanded diameter being greater than the unexpanded diameter. In other embodiments, the sheath may be comprised of an inelastic material such that the diameter of the sheath lumen in the unexpanded diameter and the expanded diameter are about the same.

The sheath may be constructed from any suitable biocompatible material. Preferably, the sheath comprises a polymeric material. In one embodiment, the sheath may be comprised of an elastomeric material. Suitable elastomeric materials include, but are not limited to, polyurethane-based elastomer, polyester-based elastomer, polyolefin-based elastomer, polyamide-based elastomer, polystyrene-based elastomer, fluorine-based elastomer, silicone rubber, fluororubber, and latex rubber. In another embodiment, the sheath may be comprised of a substantially inelastic material. In a preferred embodiment, the sheath may be comprised of an inelastic material such that length of the sheath may not change substantially as lumen 120 contracts and expands as devices are delivered therethrough. In one preferred embodiment, the sheath may comprise expanded polytetrafluoroethylene (ePTFE). In some embodiments, the sheath can be coated with one or more materials as needed. For example, the sheath may be coated with a hydrophilic or lubricous material to facilitate advancement of the endoscope and sheath through the patient anatomy.

Figure 2:
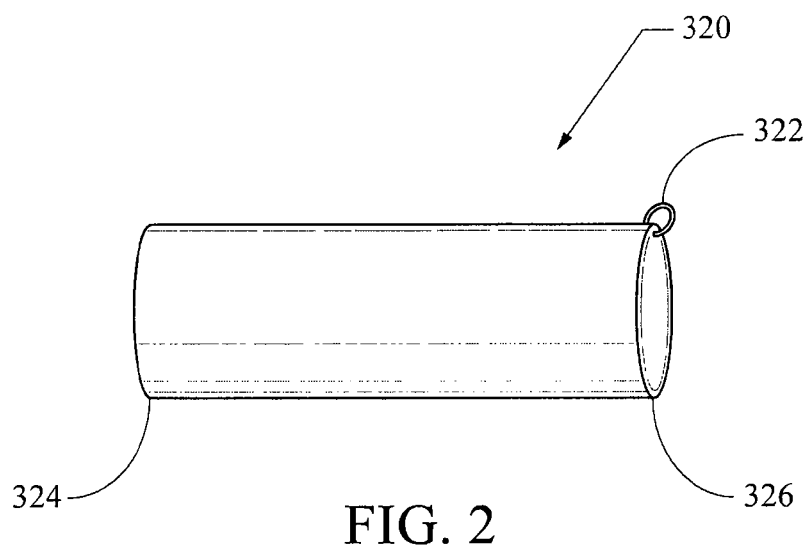
FIG. 2 depicts medical device 320.

FIG. 2 depicts a device 320 that may be delivered to a selected target anatomy using sheath 100. As shown, device 320 is intended to be a generic representation of any device that may advanced down sheath lumen 120. The device may be pushed down the sheath lumen, optionally with the aid of a pushing catheter or other similar device; the device may be pulled down; or the device may be both pushed and pulled down the lumen. Device 320 may be a device adapted to provide therapy or diagnosis to the selected target anatomy, or alternatively, a device configured to deliver another therapeutic or diagnostic device to the selected target anatomy. Device 320 may be, for example, a nasoenteric tube, a J portion of a PEG-J tube, a colon decompression tube, a biliary stent, a delivery catheter, an overtube, an introducer sheath, or another device. Device 320 includes a proximal end 324 and a distal end 326. In some embodiments, as will be explained in greater detail below, device 320 may have a coupling element 322 complimentary to and configured to couple with another coupling element. In other embodiments, coupling element 322 may be absent from device 320.

Figure 3:
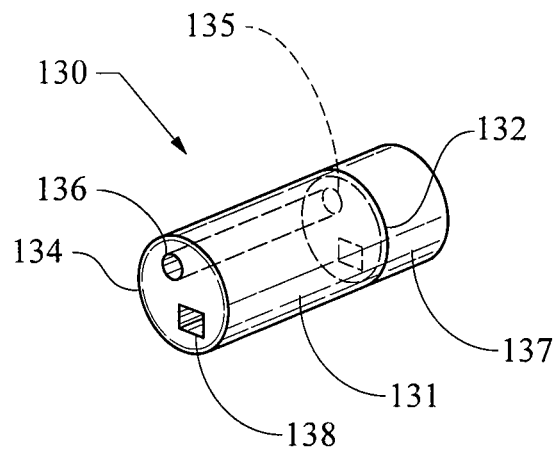
FIG. 3 depicts endoscope cap 130.

FIG. 3 depicts an endoscope cap 130 that may be configured to engage the distal end of the sheath. Cap 130 may be detachable from the sheath, or alternatively, may be integral therewith. The cap may be a tubular structure including a body 131 having a proximal end 132, a distal end 134, and an aperture 135 configured to receive the distal end of an endoscope. The distal end 134 may have apertures 136 and 138 configured to align with an endoscope working channel and visualization device, respectively.

In some embodiments, the cap may be configured to fit over the distal end of sheath 100. For example, the cap may be configured to a diameter such that the cap tightly fits over the distal end of the endoscope and sheath. A cap comprised of a thermoplastic elastomer may be particularly suited to such embodiments. Cap 130 may include a frictional inner diameter surface configured to further secure the cap to the endoscope and sheath. In another embodiment, the cap may be fixedly attached to the distal end of the sheath. For example, the cap may be attached to the distal end of the sheath via an ultrasonic welding process. In other embodiments, the cap may include adhesive, magnets, a detent structure, or other suitable structures and materials configured to fixedly or temporarily attach cap 130 to sheath 100.

In some embodiments, the cap 130 may include an engagement portion 137 configured to secure the cap to the endoscope and sheath. The engagement portion may be integral with or attached to proximal end 132 of the cap. The engagement portion, which preferably extends proximally from body 131, may be constructed from a flexible material that provides a frictional inner diameter surface. For example, the engagement portion may be constructed of a polyurethane that is molded to body 131. In other embodiments, it may be constructed from, for example, silicone or another soft polymer that will provide an ability to mount and frictionally (but removably) attach cap 130 to the endoscope and sheath.

Body 131 may be constructed of rigid material(s). In some embodiments, all or a portion of the body may be generally transparent. For example, the body may be constructed of a clear polycarbonate polymer. Alternatively, it may be constructed of another clear, translucent, or opaque polymer such as polyurethane, acrylic, or nylon. Body 131 preferably is dimensioned such that its outer diameter is about the same as the outer diameter of the endoscope on which cap 130 is to be used. For example, body 131 may have an outer diameter of about 8.5 mm to about 12 mm for use with endoscopes having those outer diameters. The skilled artisan will appreciate that body 131 may be dimensioned appropriately for use with endoscopes having greater or lesser diameters, and it may also have a cross-section configured for use with a similarly-shaped endoscope.

Figure 4A:
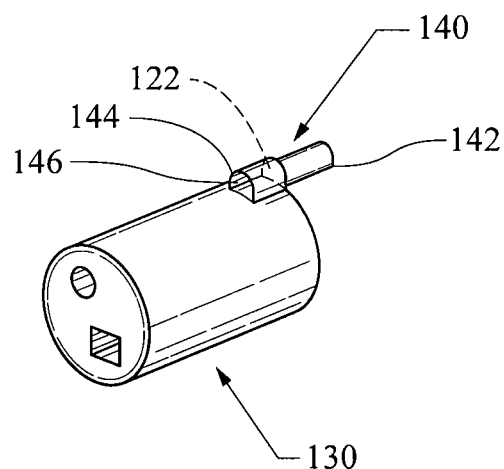
FIG. 4A depicts endoscope cap 130 with coupling member 140.
Figure 4B:
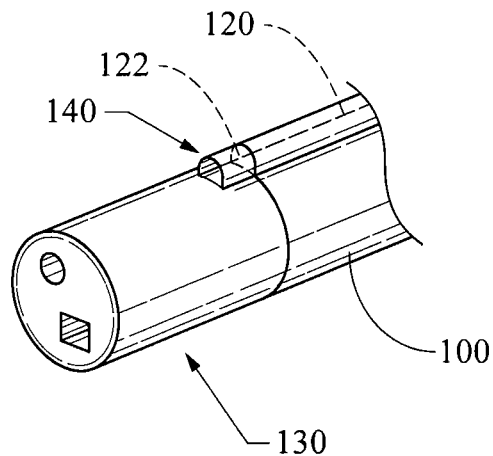
FIG. 4B depicts endoscope sheath 100 and endoscope cap 130.

FIG. 4A depicts endoscope cap 130 further including a coupling member 140 configured to mate with lumen 120 at aperture 122. The coupling member may provide stress relief in the sheath lumen, and thus prevent the sheath from tearing during delivery of devices therethrough. In particular, as a device is advanced down lumen 120, with coupling member 140 in place, the device advances from lumen 120 into lumen 146, and thereafter exits into the patient anatomy. The coupling member includes a proximal end 142, a distal end 144, and a lumen 146 extending from proximal end 142 to distal end 144. Coupling member 140 may be configured to frictionally engage the inner surface of lumen 120 near aperture 122. Alternatively, where the endoscope cap is fixedly attached to the sheath, coupling member 140 may be fixedly mated with lumen 120. For example, proximal end 142 may be attached to the lumen 120 at aperture 122 with adhesive, with ultrasonic welding, or another suitable material or method as is known in the art. FIG. 4B depicts endoscope cap 130 mated with sheath 100, wherein coupling member 140 is mated with lumen 120.

Figure 5:
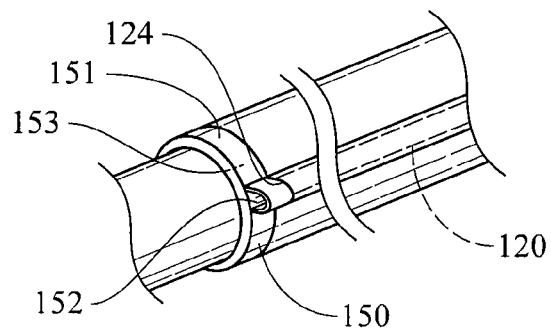
FIG. 5 depicts endoscope sheath 100 with coupling member 150.

Optionally, the sheath may include another coupling member 150 mated or configured to mate with lumen 120 at aperture 124. FIG. 5 depicts coupling member 150 mated with proximal portion 102 and lumen 120 at aperture 124. Coupling member 150 includes a body 151 having a lumen 153 for the endoscope, and a lumen 152 through which a device may be inserted and thereafter advanced through lumen 120 toward the distal portion of the endoscope. Similarly to endoscope cap 130, coupling member 150 may be configured to be detachable from the sheath or may be integral therewith. The coupling member may include suitable structural elements to secure the member to the endoscope and sheath, such as those already described herein. For example, in one embodiment, coupling member 150 may be integral with the proximal end of the sheath, and may be configured to frictionally engage a proximal portion of the endoscope. Optionally, where cap 130 is absent from the endoscope sheath, the sheath may include a coupling member 150 mated or configured to mate with lumen 120 at aperture 122 wherein a device advanced down lumen 120 may enter lumen 153 and thereafter exit into the patient anatomy.

Figure 6A:
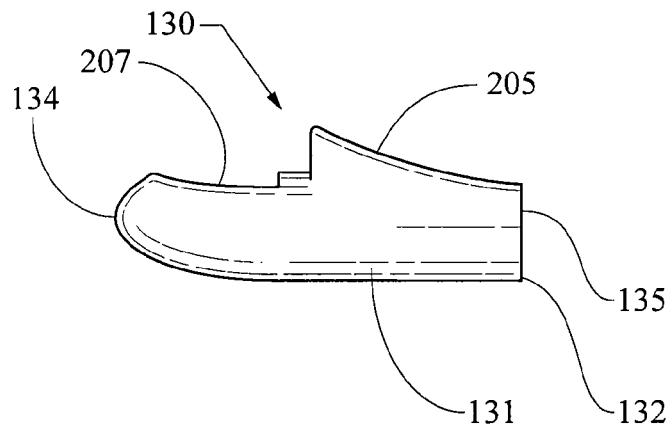
FIGS. 6A-6C depict endoscope cap 130 with ramp 205.
Figure 6B:
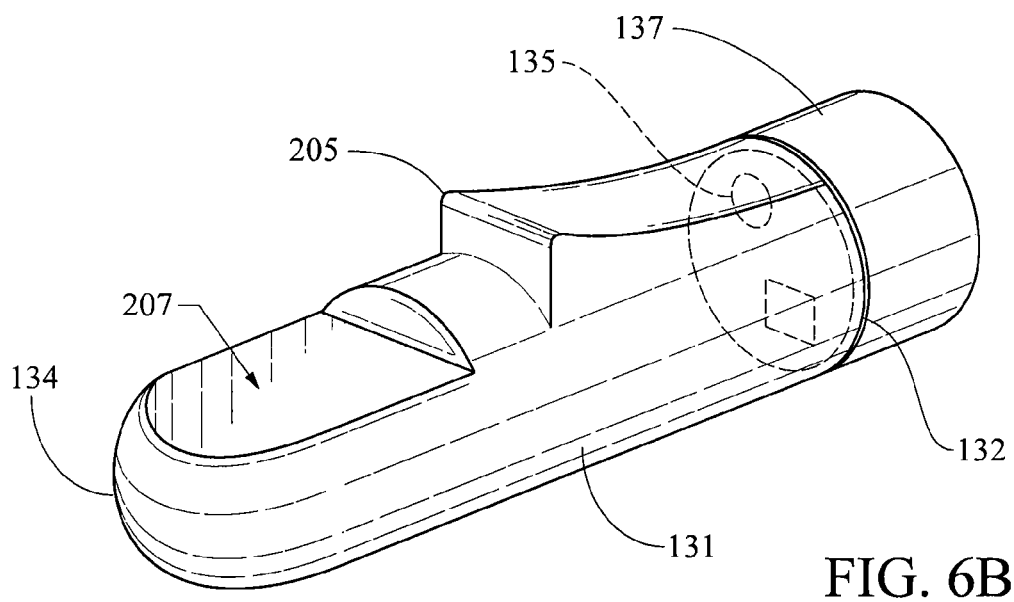
Figure 6C:
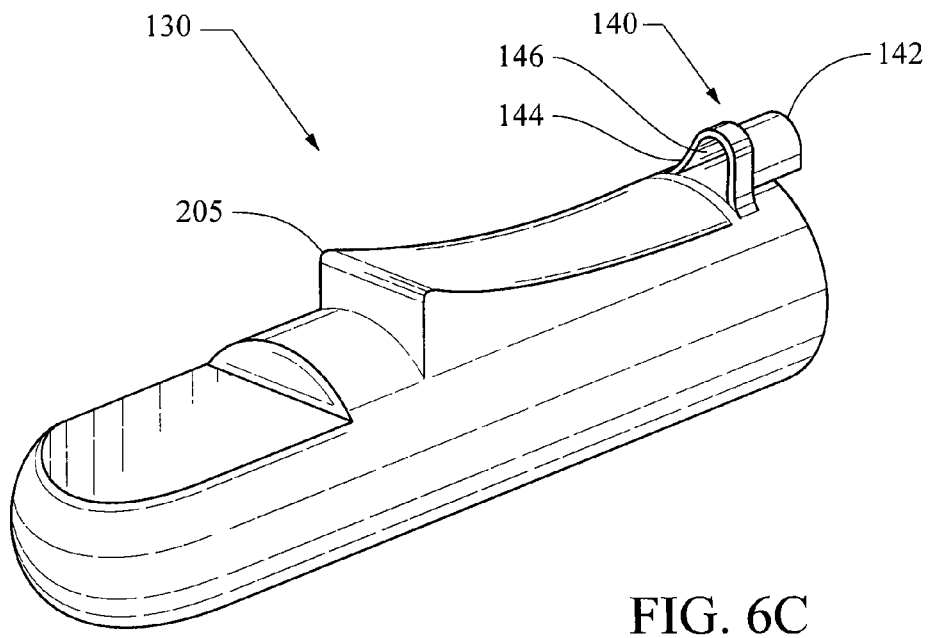
Figure 6D:
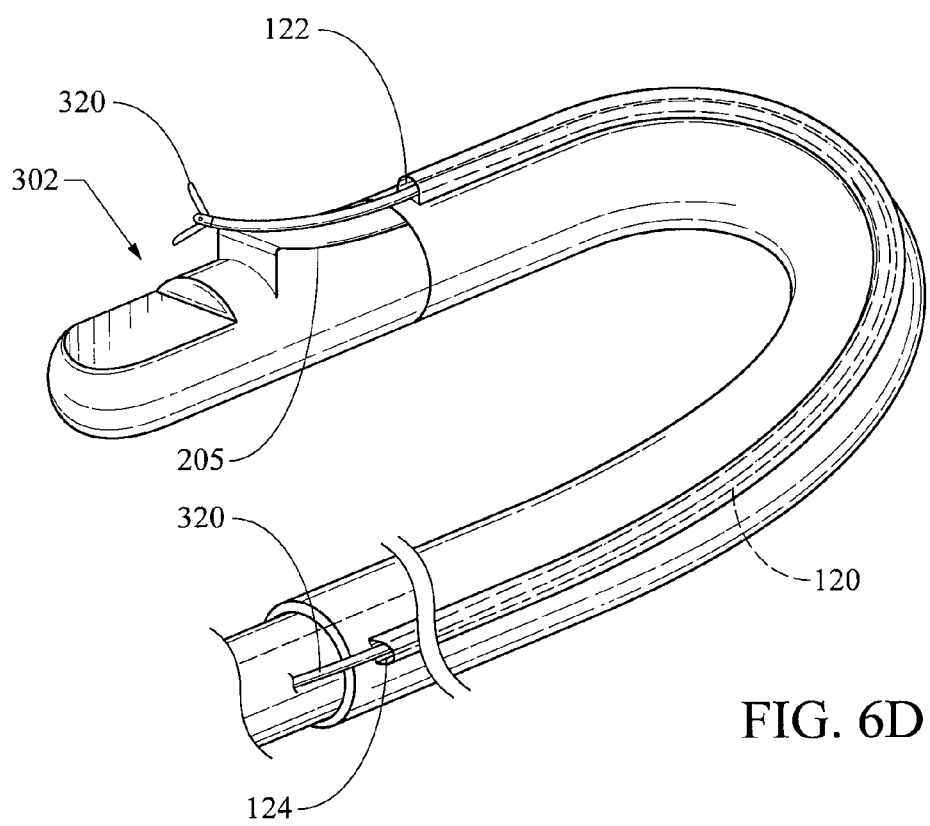
FIG. 6D depicts device 320 delivered through endoscope sheath 100.

FIGS. 6A-6C depict endoscope cap 130 configured for a duodenoscope wherein the cap includes a ramp 205 that can be used to deflect medical devices toward a selected target anatomy. The cap also includes a side aperture 207 configured to accommodate the endoscope's visualization devices (e.g., camera, CCD, or fiber-optic element) and working channel(s). The cap may also include coupling member 140 as described above and depicted in FIG. 6C. As an illustrative example, FIG. 6D depicts use of sheath 100 and endoscope cap 130 to deliver a grasping device 320 to the distal end of an endoscope. As shown, device 320 has been pushed down lumen 120 and thereafter deflected by ramp 205.

The ramp 205 may be configured to a variety of angles of elevation relative to the body 131. In general, however, the ramp presents an angle of elevation ranging from about 1 degree to about 90 degrees relative to body 131, preferably about 5 degrees to about 75 degrees, more preferably about 10 degrees to about 60 degrees, and most preferably about 20 degrees to about 45 degrees. The ramp incline surface may be a uniform planar surface, or alternatively, may be a curvilinear surface. Preferably, the ramp surface is atraumatically shaped. For example, ramp 205 as shown in FIG. 6A presents an atraumatic profile with rounded edges along the ramp surfaces. In some embodiments, the ramp may comprise surface structures configured to receive a device delivered down the sheath. For example, ramp 205 may comprise a grasping slot configured to grasp a device delivered through lumen 120. The grasping slot may take on any suitable shape or form for grasping device 320. Suitable grasping configurations are disclosed in U.S. Patent Application Publication No. 2007/0208219, and may be applied to the presently disclosed ramps.

The ramp may be comprised of any suitable biocompatible material(s). In some embodiments, the ramp may be comprised of the same material as body 131. In other embodiments, the ramp may be comprised of a different material from body 131 or a combination thereof. Preferably, the ramp is comprised of a polymeric material. Properties of the ramp, such as flexibility/rigidity, may be adjusted by selection of an appropriate polymer as is known in the art. For example, polymers with a low coefficient of friction may be particularly suitable for various embodiments, while polymers with a high coefficient of friction may be suitable in other embodiments, such as for ramps configured to grasp a delivered device. Suitable polymeric materials include, but are not limited to, polytetrafluorethylene, polyethylene, ultra-high molecular weight polyethylene, polypropylene, perfluoroelastomer, fluoroelastomer, nitrile, neoprene, polyurethane, silicone, styrene-butadiene, rubber, polycarbonate, acrylic, nylon, or combinations thereof.

Figure 7:
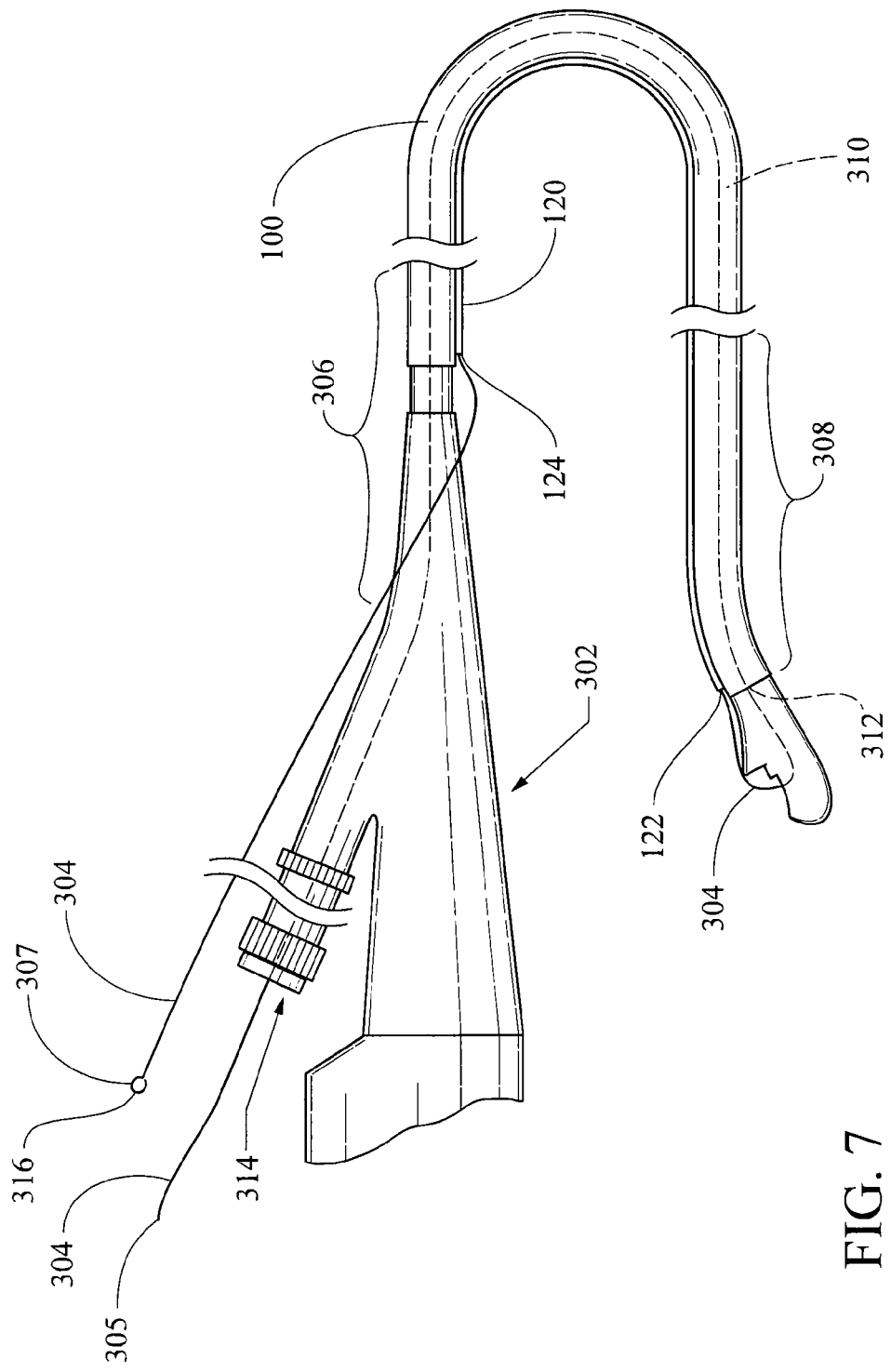
FIG. 7 depicts endoscope sheath 100 and a tether system.

FIG. 7 shows sheath 100 disposed on endoscope 302 wherein the endoscope includes a tether system. The tether system may be used to pull devices down alongside the endoscope from proximal portion 306 to distal portion 308. Endoscope 302 has a working channel 310 extending from proximal portion 306 to distal portion 308. The working channel connects to an aperture 312 disposed at distal portion 308. Tether 304 extends alongside the endoscope through lumen 120 from the proximal portion 306 to the distal portion 308 and enters working channel 310 via aperture 312. The tether extends back through the working channel to proximal portion 306 and exits at port 314. The tether includes a first end 305 and a second end 307. The tether may include a coupling element 316, preferably located at second end 307. The coupling element may be attached to or integrally formed with tether 304. The coupling element may be attached to the tether by glue, adhesive, or suture, for example. Once endoscope 302 has reached a selected target anatomy and device 320 has been coupled to the tether, device 320 may be advanced to the distal portion of the endoscope by pulling the tether back through working channel 310 from port 314. Preferably, device 320 can be pushed from its proximal end 324 while the tether is used to pull from its distal end 326.

Figure 8:
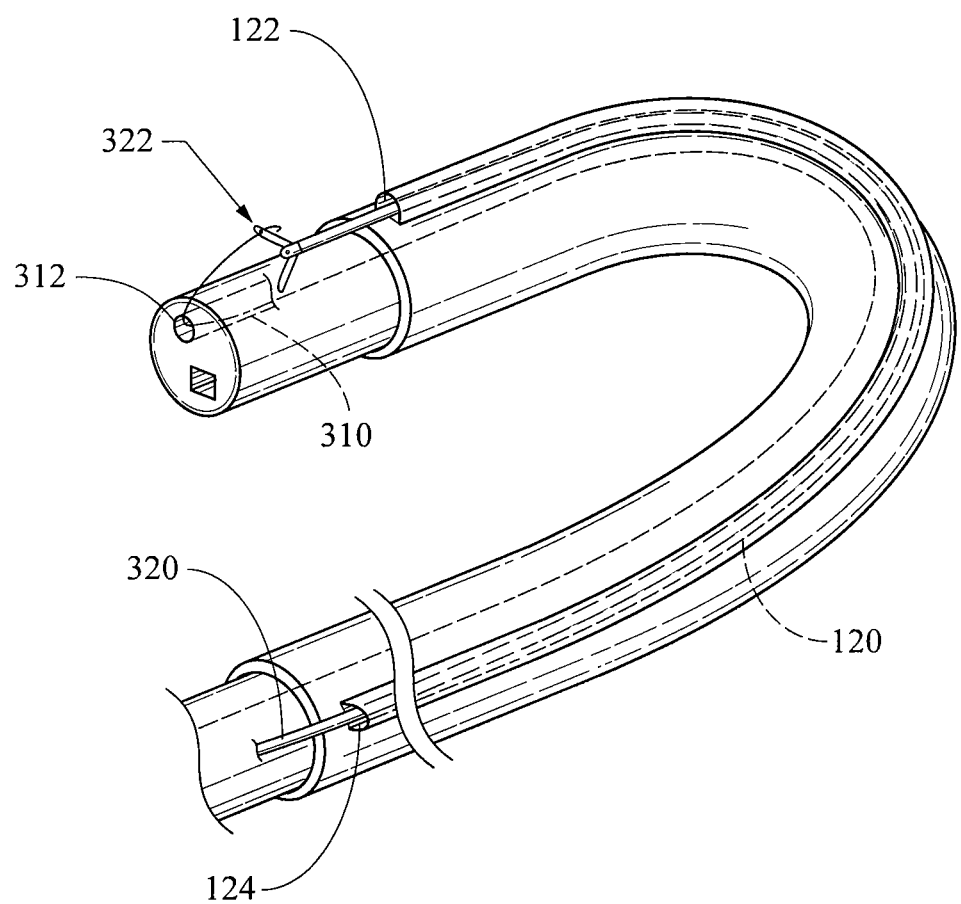
FIG. 8 depicts device 320 delivered through endoscope sheath 100.

In one exemplary embodiment, FIG. 8 shows a grasping device 320 that has been advanced down lumen 120 using the tether system. Grasping device 320 includes a coupling element 322 integral with the device. The grasping device extends from proximal portion 306 to aperture 124, through lumen 120, and exits aperture 122. After delivery to distal portion 308, as will be explained in greater detail below, device 320 may be decoupled from the tether and the tether can be pulled back into working channel 310. The grasping device may then be used to perform various functions in the patient anatomy as is known in the art. Introducing device 320 with sheath 100 minimizes mucosal trauma to tissue surrounding the path of introduction.

Tether 304 may be a strap, a wire, a suture, a thread, or any other device capable of functioning as a tether suitable for the intended use. Preferably, the tether is configured to bend without kinking. In cases where additional instruments will be introduced through the endoscope working channel or where the working channel will be used to provide aspiration or decompression, preferably the tether occupies minimal space therein and does not substantially interfere with the procedure. In one embodiment, the tether may be a wire having a 0.035 millimeter diameter, and can be used with an endoscope having a lumen diameter of 4.8 millimeters, for example. In another embodiment, the tether may be a flexible strap, such as a nylon strap, configured to conform to an inner surface of the endoscope working channel. The tether may be fabricated from a variety of biocompatible materials, including metal alloys and polymeric materials. Suitable polymeric materials include, for example, nylon, polyester, polyethylene, ultra-high molecular weight polyethylene, or polypropylene. Suitable metal alloys include, for example, nickel-titanium alloys. The tether can be coated with one or more materials. Preferably, at least a portion of the tether is coated with a hydrophilic or other lubricious material that can facilitate advancement of the tether through the anatomy of the patient. The tether may be coated with, for example, SLIP-COAT® Biopolymer, STS Biopolymers, Inc., Henrietta N.Y.

The coupling elements 316 and 322 may include any suitable structures configured to temporarily couple two medical devices. For example, the coupling elements may include a closed loop structure as depicted in FIGS. 2 and 7. The coupling elements may include releasable or breakable sutures, temporary or dissolvable bonds or adhesives, magnets, or a combination thereof. The coupling elements may include a biocompatible ball which is crimped, glued, or otherwise designed to slide off or break apart with the application of sufficient amount of pull force (e.g., 3 pounds), and can thereafter be safely passed through the gastrointestinal system or be absorbed thereby. Optionally, device 320 may be coupled directly to the tether, with for example, breakable or dissolvable sutures.

The tether system may further include a guiding device used to advance devices beyond the distal portion of the endoscope (FIGS. 9A-9E). Guiding device 400 includes a flexible or semi-flexible elongate member 402, a fulcrum 404, and a variable stiffness cable 406. The elongate member 402 includes a distal portion 410 and a proximal portion 412. The elongate member may have a range of lengths and diameters depending on the size of the working channel of the endoscope to be used and the procedure to be performed. In general, the length of elongate member 402 ranges from about 100 cm to about 300 cm. The cross-sectional diameter generally ranges from about 1 mm to about 3 mm, and is preferably configured for advancement through the working channel of the endoscope. The skilled artisan will appreciate that all dimensions provided herein are intended as examples only, and guiding devices having different dimensions may be substituted for a particular use.

Elongate member 402 includes a biocompatible material that encases variable stiffness cable 406, shielding it from direct exposure to the patient anatomy. The material may be, for example, expanded polytetrafluoroethylene, polytetrafluoroethylene, polyethylene, or polyurethane. In one exemplary embodiment, elongate member 402 may be fabricated by placing heat shrink tubing, such as heat shrink polytetrafluoroethylene tubing, over the variable stiffness cable 406 and thereafter heat shrinking the tubing in place. The elongate shaft may comprise one or more materials providing the shaft with properties of sufficient strength, flexibility, and resistance to compression in order to traverse tortuous areas of the anatomy. Such materials include nylon, polyether block amides, polyethylene terephthalate, polytetrafluoroethylene, polyetheretherketone, or combinations thereof. The skilled artisan will appreciate, however, that the elongate member may be constructed from other biocompatible materials as is known in the art to provide the desired properties.

Figure 9A:
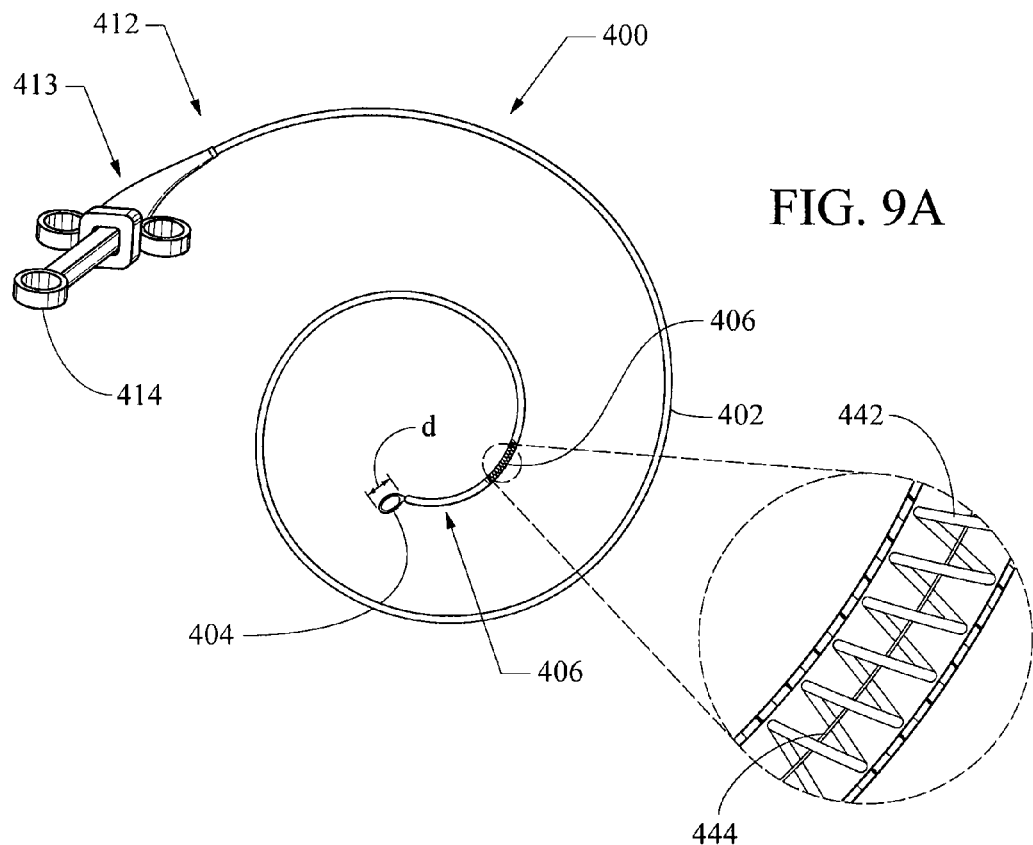
FIGS. 9A-9C depict guiding device 400.
Figure 9B:
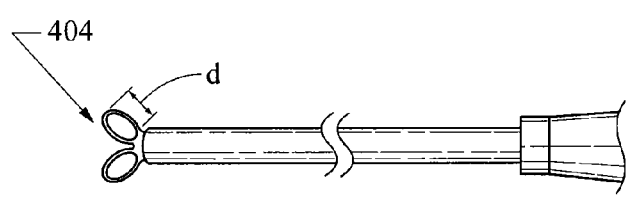
Figure 9C:
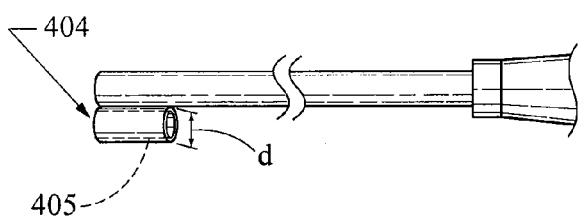

Fulcrum 404 is attached to or integrally formed with distal portion 410 of elongate member 402. The fulcrum may be any suitable structure configured to receive tether 304 and provide a point at which the tether can be advanced through or around. Fulcrum 404 may be, for example, a single loop structure (FIG. 9A), a double loop structure (FIG. 9B), or a cylindrical structure having a lumen 405 extending therethrough (FIG. 9C). The fulcrum has a diameter d preferably ranging from about 1 mm to about 3 mm. In some embodiments, the fulcrum may be constructed of wire, suture, or thread. In other embodiments, the fulcrum may be constructed of a more rigid material. In general, however, fulcrum 404 may comprise any material suitable for the intended use. The fulcrum may include, for example, polymeric materials such as nylon, and/or metallic materials such as nickel-titanium alloys.

Portions of the guiding device can be coated with one or more materials. Preferably, at least a portion of elongate member 402 is coated with a hydrophilic or other lubricious material. Hydrophilic or other lubricious coatings are known to facilitate advancement of devices through patient anatomy or introducer devices. In some embodiments, fulcrum 404 may be comprised of and/or coated with a material that facilitates smooth advancement of the tether therethrough. Preferred materials include polytetrafluoroethylene, ultra-high molecular weight polyethylene (UHMWPE), nylon, and polyoxymethylene.

Variable stiffness cable 406 is disposed through elongate member 402 and includes a helical spring 442 extending from proximal portion 412 to distal portion 410 near fulcrum 404. The spring includes a small pitch between the adjacent turns. A wire 444, such as a stainless steel wire, extends through the central bore of spring 442 and is affixed to the distal end thereof. Alternatively, the wire and the spring may both be affixed to a distal tip. Wire 444 is operatively connected to a hand assembly 413 located proximal to proximal portion 412. Hand assembly 413 includes an actuator 414 that can be used to compress or decompress spring 442. For example, in some embodiments, retraction of the actuator in the proximal direction retracts wire 444. This retraction of the wire reduces the distance between the turns in spring 442, and thereby reduces the spring's flexibility. Additional examples of variable stiffness cables are disclosed in U.S. Pat. Nos. 4,215,703 and 3,854,473, the disclosures of which are herein incorporated by reference in their entirety.

Figure 9D:
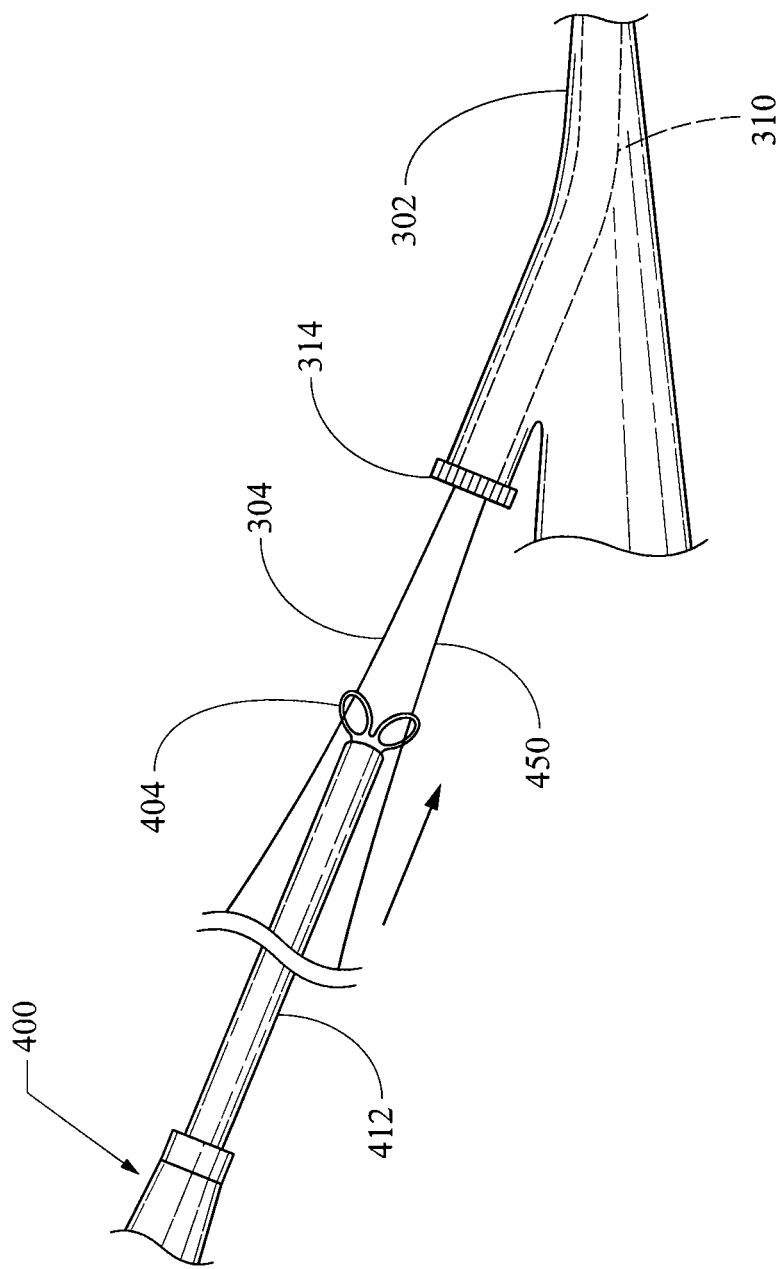
FIG. 9D depicts loading of guiding device 400 onto a tether and a wire guide.

Guiding device 400 may be loaded onto tether 304 at the proximal portion of the endoscope by passing first end 305 of tether 304 through fulcrum 404. Preferably, the guiding device is also loaded onto the proximal end of a wire guide 450 that exits port 314 and has been used to cannulate the target anatomy. The tether and the wire guide may be passed, for example, through the double loop fulcrum 404, as depicted in FIG. 9D. The elongate member 402 can then be advanced into the working channel 310 via port 314. Thereafter, the elongate member may be advanced through the working channel, out apertures 312, and to a selected target anatomy beyond distal portion 308. In some embodiments, an endoscopic elevator apparatus may be used to aid in advancement of elongate member 402 into the selected target area. As the elongate member advances beyond the distal portion of the endoscope, preferably the tether becomes looped around the fulcrum and is pulled into the target anatomy.

Figure 9E:
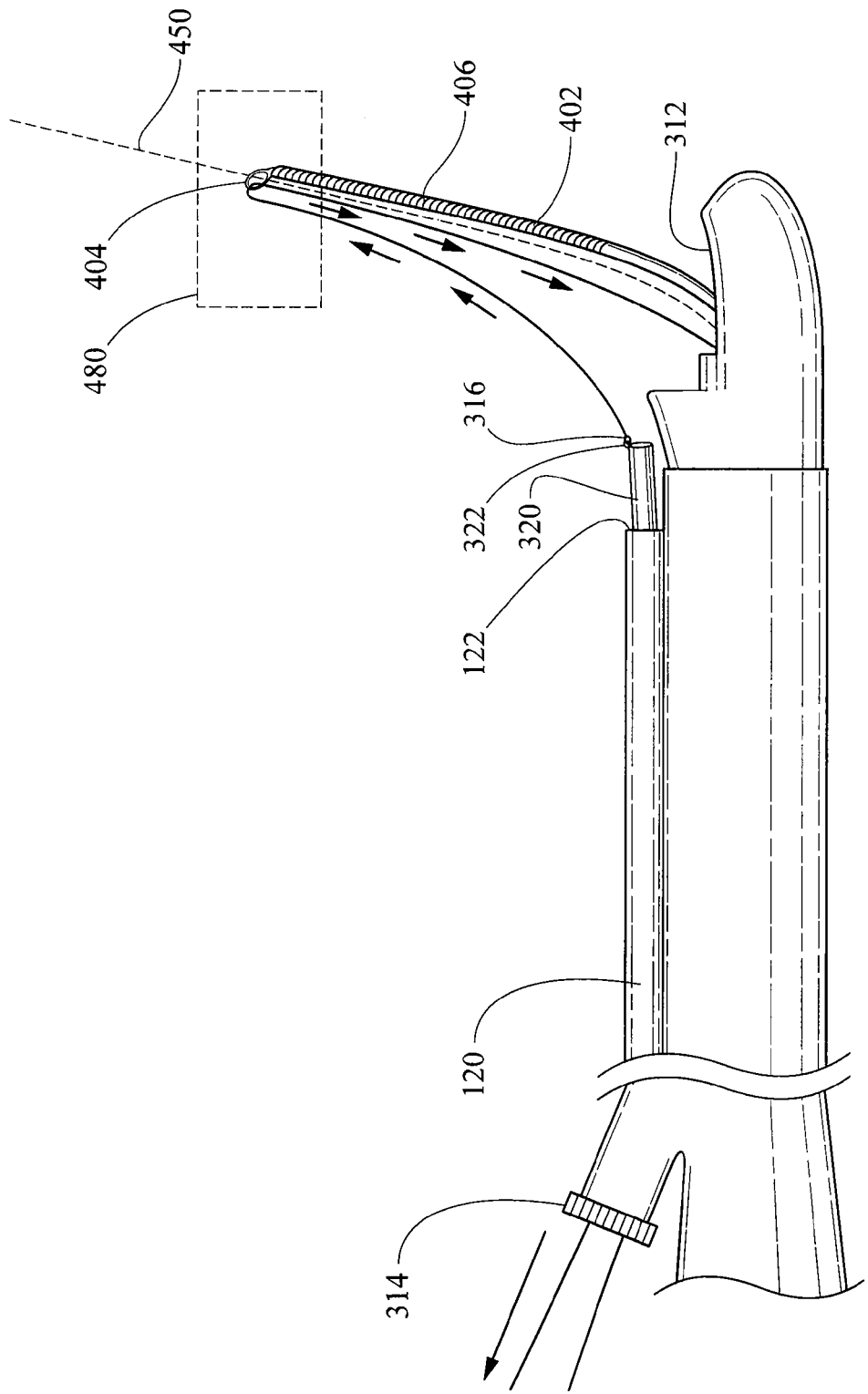
FIG. 9E depicts endoscope sheath 100 and guiding device 400.

Once distal portion 410 of elongate member 402 reaches a target anatomy 480, the variable stiffness cable 406 may be used to stiffen and anchor the elongate member in place (FIG. 9E). The tether can then be pulled back through working channel 310 from port 314, thereby advancing a coupled device 320 through lumen 120 toward distal portion 308. Upon reaching the distal portion of the endoscope, device 320 may advanced toward the target anatomy.

During introduction of the endoscope and extension of the guiding device into the target anatomy, the tether can be held secure as needed. Preferably, the tether is long enough so that control can be maintained at both ends while the endoscope and guiding device are advanced to the target anatomy. In other words, preferably the tether is greater than two times the length of the endoscope. In embodiments using the guiding device, preferably the tether is greater than two times the additive length of the endoscope and the length of the portion of elongate member 402 that extends out of aperture 312 and to the target anatomy. The portion of tether exiting port 314 can be held secure at the port by, for example, a locking device (e.g., Fusion® Wire Guide Locking Device, Cook Endoscopy Inc., Winston-Salem, N.C.), or by holding the tether. Likewise, the other end of the tether, specifically the portion of tether extending through lumen 120 back to proximal portion 306, can be held secure by a locking mechanism or similar device, or by holding the tether. As elongate member 402 or device 320 is advanced into the target anatomy, the tether can be unlocked as needed.

FIGS. 10A-10F demonstrate a method by which a medical device can be introduced alongside the endoscope to a selected target anatomy. In one exemplary embodiment, endoscope sheath 100 can be used with Endoscopic Retrograde Cholangiopancreatography (ERCP). ERCP involves inserting a duodenoscope into a patient's mouth and through the esophagus, stomach, and duodenum until it reaches the area where the ducts of the biliary tree and the pancreas open into the duodenum. Devices delivered through the endoscope's working channel may then traverse the Papilla of Vater for access to the ductal system. Therein, these devices can be used to perform diagnostic and therapeutic procedures. Examples of such devices include wire guides, baskets, snares, stents, extraction balloons, introducer brushes, catheters, and baby endoscopes usually of 0.8 mm to 4 mm in diameter.

One ERCP procedure includes delivery of a plastic biliary stent into an area of the bile or pancreatic duct where a stricture is blocking drainage of fluid. The blockage may be caused by a tumor in the bile or pancreatic duct. Typically, by the time symptoms appear in the patient, the tumor is at an advanced stage and is deemed inoperable. As a result, management of the cancer usually focuses on palliation of the symptoms. As an alternative to surgical bypass procedures for palliation, a stent may be delivered by ERCP and positioned through the obstructed area so as to maintain a pathway for fluid to flow across. However, the maximum diameter of a plastic biliary stent generally depends on the diameter of the endoscope's working channel. As a result, in some instances multiple stents must be placed within the stricture to allow for sufficient drainage. Using the presently disclosed endoscope sheath, plastic biliary stents having diameters larger than the endoscope's working channel can be delivered to the bile or pancreatic ducts. These larger tubes may facilitate more efficient drainage of the duct and may be less prone to clogging compared to their smaller counterparts.

Figure 10A:
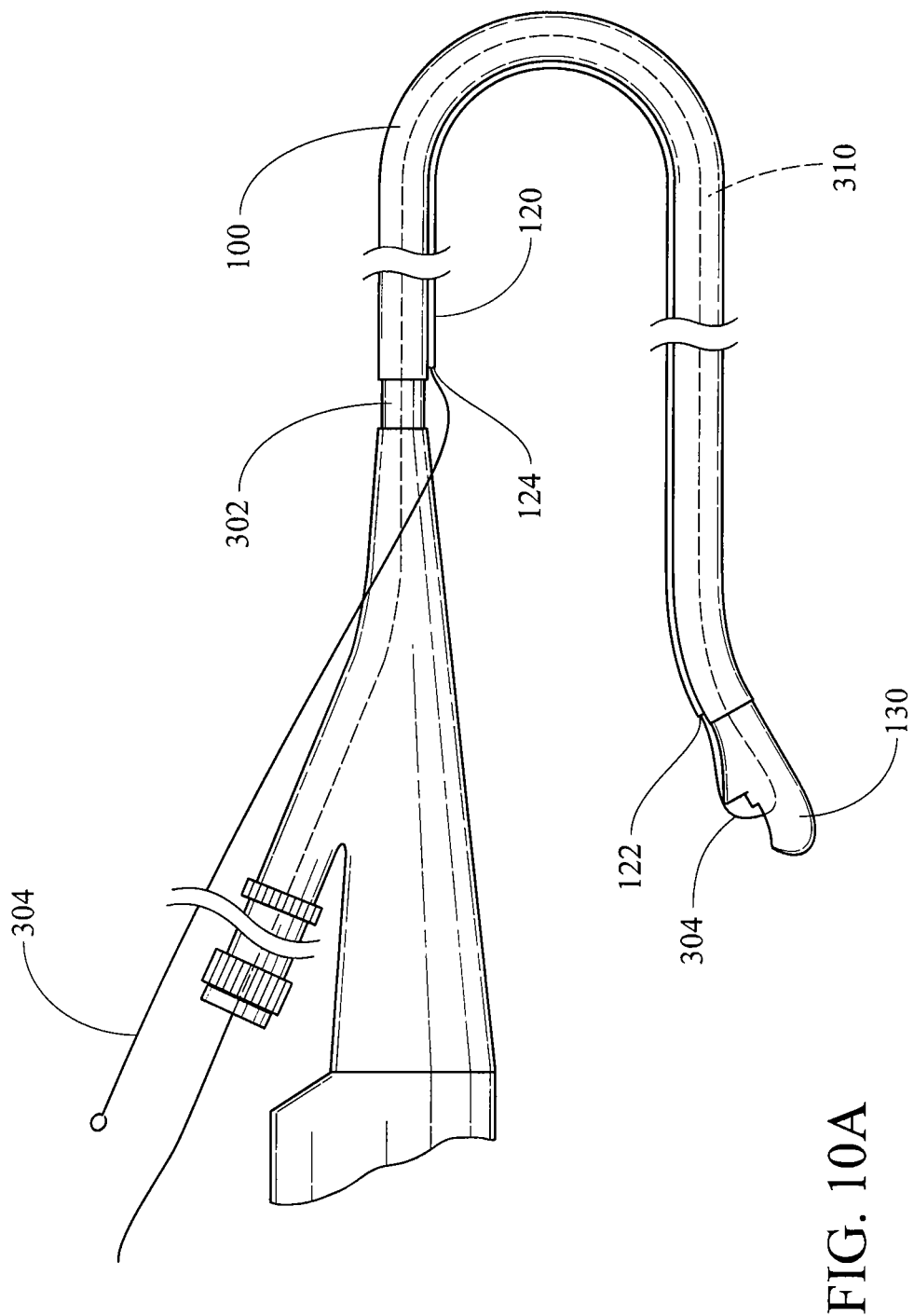
FIGS. 10A-10F depict delivery of a large plastic biliary stent into the common bile duct using endoscope sheath 100.
Figure 10B:
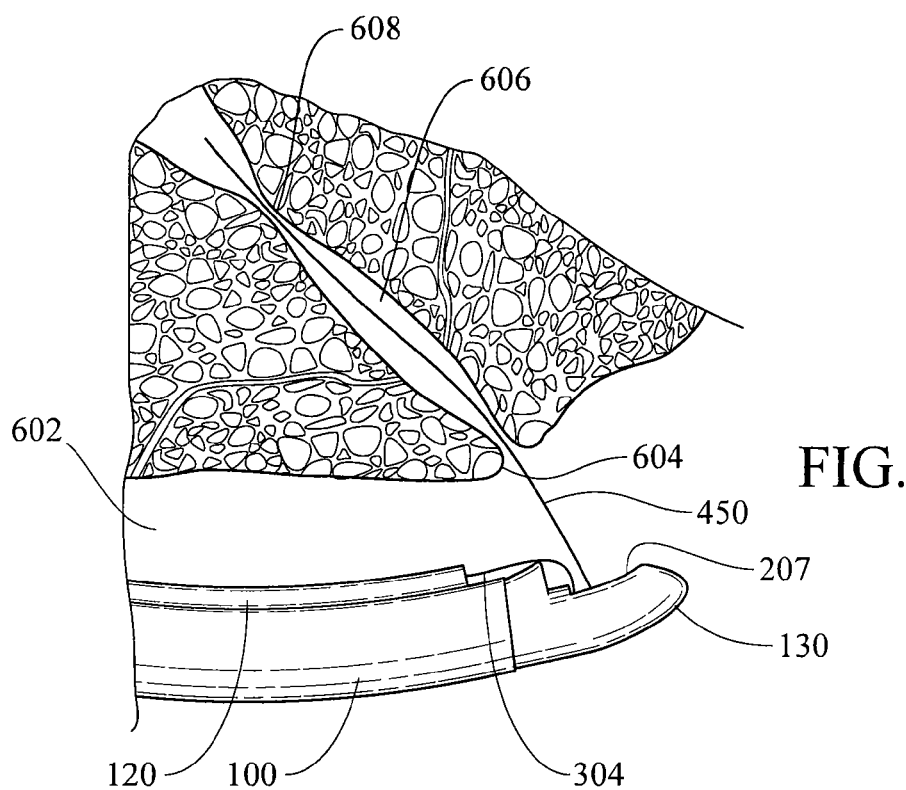
Figure 10C:
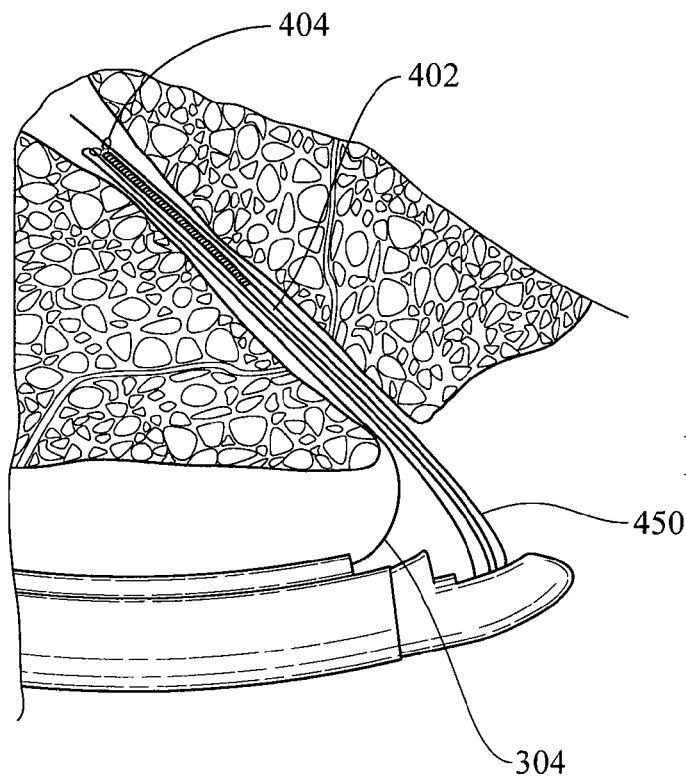

FIGS. 10A-10F illustrate delivery of a large plastic biliary stent 610 into the common bile duct using sheath 100. The tether 304, guiding device 400, and cap 130 with ramp 205 are also used to deliver the stent. The procedure begins with the tether disposed through lumen 120 and back through lumen 310, as depicted in FIG. 10A. The endoscope may then be advanced into the patient and positioned in the duodenum 602 to allow viewing of the Sphincter of Oddi and the Papilla of Vater 604, which lie at the opening to the common bile duct 606 and the pancreatic duct. Next, the wire guide 450 may be extended out of apertures 207 and 312, through the Ampulla of Vater and into the ductal system (FIG. 10B). Preferably, the wire guide is advanced past the stricture 608. A dilator catheter may be used as needed to facilitate cannulation of the duct. A more detailed description of cannulation of the common bile duct with the assistance of a dilator catheter is disclosed in U.S. Patent Application Publication No. 2005/0059890, the disclosure of which is herein incorporated by reference in its entirety. The guiding device 400 can be loaded over the wire guide and the tether 304 at the proximal portion of the endoscope. Elongate member 402 of the guiding device may be advanced through the endoscope's working channel and thereafter extended out of apertures 207 and 312 and into the ductal system, all the while advancing over the wire guide via fulcrum 404 (FIG. 10C). The endoscope may include an elevator apparatus that may be used to deflect the guiding device toward the ductal system. As elongate member 402 advances into the ductal system, the tether will also be advanced by virtue of its contact with fulcrum 404. Preferably, fulcrum 404 is advanced past stricture 608 so that the biliary stent can be pulled into place when advanced into the target anatomy. Once elongate member 402 is advanced to the desired location, variable stiffness cable 406 may be engaged by manipulation of actuator 414, thereby causing stiffening of the elongate member 402. Stiffening anchors the elongate member in position and provides rigidity which can prevent buckling during delivery of device 320.

Figure 10D:
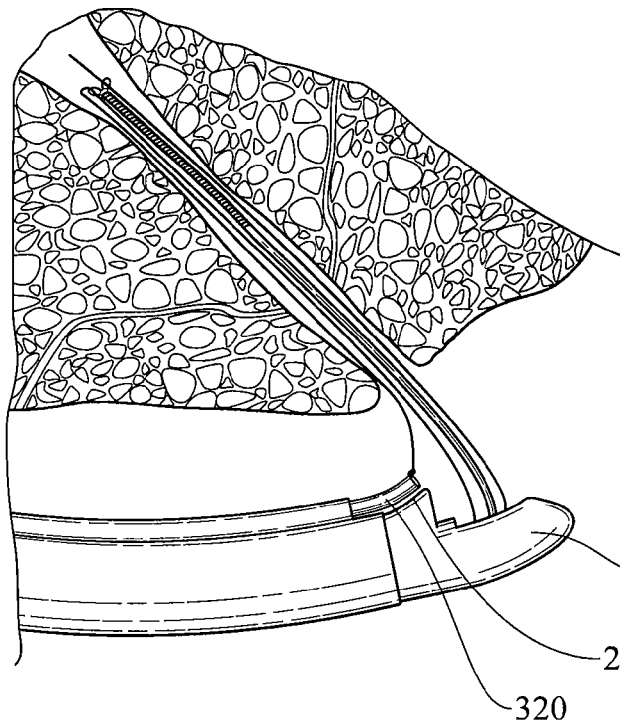

Next, the biliary stent may be coupled to the tether at the proximal portion of the endoscope. Preferably, the stent is loaded into and delivered via a delivery catheter that is configured to couple to the tether. The delivery catheter, as device 320, includes a coupling element 322 for coupling to the tether, and preferably includes a stiffening element or a partially rigid portion so that the catheter can be pushed from its proximal end 324. Pushing the stent or the delivery catheter can reduce tension on the tether during introduction and may reduce the incidence of mucosal trauma. Once coupled, device 320 may be advanced into lumen 120 at aperture 124. Device 320 may then be advanced through lumen 120 and thereafter to the distal portion of the endoscope. Upon exiting lumen 120 at aperture 122, preferably device 320 is deflected by ramp 205 toward the Papilla of Vater 604 (FIG. 10D).

Figure 10E:
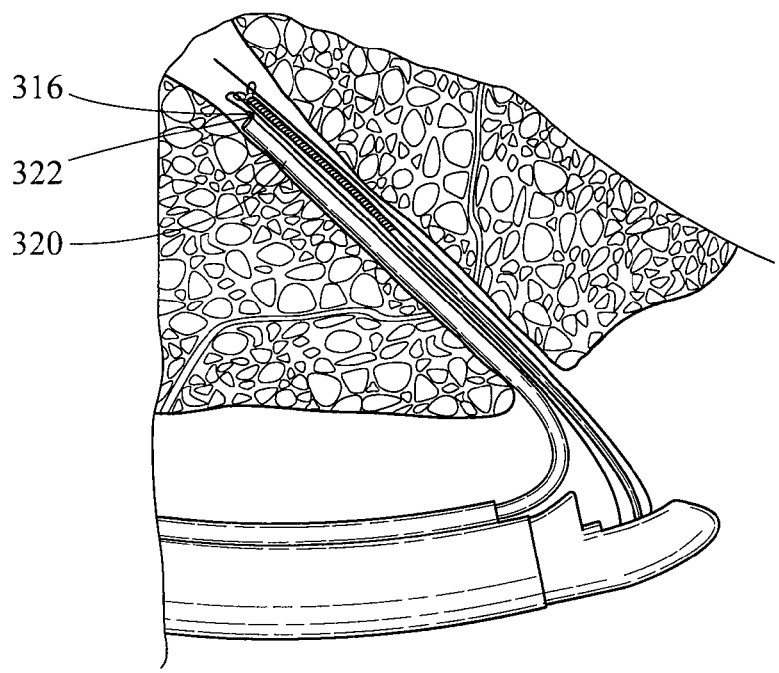
Figure 10F:
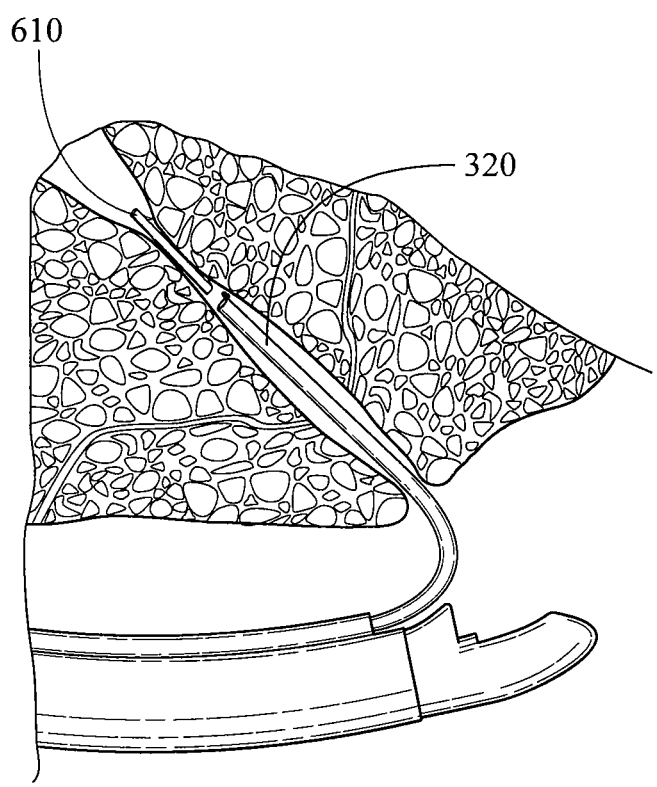

The delivery catheter may be advanced along elongate member 402 of guiding device 400 by continuing to push from the proximal end while pulling with tether 304. Preferably, the delivery catheter is advanced to distal portion 410, and thus, the target anatomy (FIG. 10E). Once the delivery catheter reaches the target site (i.e., the stricture), it may then be decoupled from the tether. For example, the delivery catheter may be held at the proximal end while the tether is pulled back at port 314 with sufficient force to detach coupling element 316 from coupling element 322, thereby decoupling the delivery catheter from the tether. The tether may then be pulled out of the ductal system and back into the endoscope working channel 310. The guiding member 400 and subsequently the wire guide 450 may be advanced out of the ductal system and back into the endoscope. Next, the biliary stent 610 may be delivered to the site of the stricture 608 by pushing the stent out of the delivery catheter using an internal pushing catheter (FIG. 10F). The delivery catheter may then be removed from the patient anatomy. The skilled artisan will appreciate that the steps of accessing, delivering, decoupling, and removal of devices from the target anatomy may be varied as necessary. For example, if additional procedures are to be performed using the wire guide, it may be preferable to only partially retract the wire guide from the bile duct.

While various embodiments of the invention have been described, it will be apparent to those of ordinary skill in the art that many more embodiments and implementations are possible within the scope of the invention. Accordingly, the invention is not to be restricted except in light of the attached claims and their equivalents.

The invention claimed is:

1. An advancing system, comprising:
an endoscope having a proximal portion, a distal portion, a working channel extending from the proximal portion to the distal portion, an endoscope aperture disposed at the distal portion and in communication with the working channel, and a port disposed at the proximal portion and in communication with the working channel;
an endoscope sheath having a first lumen extending along a first length from a first proximal end to a first distal end, wherein the endoscope is disposed through the first lumen, a second lumen extending along a second length from a second proximal end to a second distal end and configured to receive an elongate medical device, the second lumen being coupled to the first lumen along a majority of the second length of the second lumen, and a first aperture and a second aperture in fluid communication with the second lumen,
wherein the first aperture is disposed at the second proximal end of the second lumen, wherein the first aperture is disposed along the proximal portion of the endoscope, wherein the second aperture is disposed at the second distal end of the second lumen, and wherein the second aperture is spaced proximally of a distal end of the endoscope; and
further comprising an endoscope cap coupled to the endoscope sheath, the endoscope cap enclosing the distal end portion of the endoscope therewithin and having a distal end that is spaced distally of the endoscope aperture, the endoscope cap comprising a non-movable ramp disposed on an outer surface thereof, the ramp being configured to deflect an elongate medical device delivered through the second lumen along an angled pathway that extends outwardly and away from a longitudinal axis of the endoscope.

2. The advancing system of claim 1 wherein the first aperture is located distal to the first proximal end, and wherein the second aperture is located proximal to the first distal end.

3. The advancing system of claim 1 wherein the endoscope sheath comprises expanded polytetrafluroethylene.

4. The advancing system of claim 1 wherein the second lumen has a diameter ranging from about 2 mm to about 30 mm.

5. The advancing system of claim 1 wherein the endoscope cap is fixedly attached to the endoscope sheath at the first distal end.

6. The advancing system of claim 1 wherein the endoscope cap is detachable from the endoscope sheath.

7. The advancing system of claim 1 wherein the endoscope cap comprises a first coupling member mated with the second lumen at the second distal end.

8. The advancing system of claim 7 wherein the first coupling member comprises:
a first coupling member proximal portion and a first coupling member distal portion; and
a first coupling member lumen extending from the first coupling member proximal portion to the first coupling member distal portion, the first coupling member lumen open at both ends, wherein the first coupling member lumen is configured to receive the elongate medical device.

9. The advancing system of claim 8 wherein the first coupling member proximal portion comprises an outer surface configured to frictionally engage an inner surface of the second lumen.

10. The advancing system of claim 7 wherein the first coupling member is comprised of a rigid material.

11. The advancing system of claim 1 wherein the endoscope sheath comprises a first coupling member mated with the second lumen at the second distal end.

12. The advancing system of claim 11 wherein the first coupling member comprises:
a body; and
a first coupling member lumen extending through the body from a first coupling member proximal portion to a first coupling member distal portion, wherein the first coupling member is comprised of a rigid material.

13. The advancing system of claim 1 wherein the endoscope sheath comprises a second coupling member mated with the second lumen at the second proximal end.

14. The advancing system of claim 13 wherein the second coupling member comprises:
a body; and
a second coupling member lumen extending through the body from a second coupling member proximal portion to a second coupling member distal portion, wherein the second coupling member is comprised of a rigid material.

15. An advancing system configured for an endoscope having a proximal portion, a distal portion, a working channel extending from the proximal portion to the distal portion, an endoscope aperture disposed at the distal portion and in communication with the working channel, and a port disposed at the proximal portion and in communication with the working channel, the advancing system comprising:
an endoscope sheath having a first lumen extending along a first length from a first proximal end to a first distal end and configured to receive the endoscope, a second lumen extending along a second length from a second proximal end to a second distal end and configured to receive an elongate medical device, the second lumen being coupled to the first lumen along the second length of the second lumen, and a first aperture and a second aperture wherein the first aperture is disposed at the second proximal end and wherein the second aperture is disposed at the second distal end and wherein the first aperture is located distal to the first proximal end, and wherein the second aperture is located proximal to the first distal end; and
an endoscope cap having a non-movable ramp, wherein the ramp comprises a concave surface that is configured to engage and deflect an elongate medical device delivered through the second lumen along an angled pathway and away from a longitudinal axis of the endoscope, and wherein the endoscope cap is configured to receive the distal portion of the endoscope.

\* \* \* \* \*